United States Patent
McGahay et al.

(10) Patent No.: US 10,483,943 B2
(45) Date of Patent: Nov. 19, 2019

(54) ARTIFICIALLY ORIENTED PIEZOELECTRIC FILM FOR INTEGRATED FILTERS

(71) Applicant: GLOBALFOUNDRIES INC., Grand Cayman (KY)

(72) Inventors: Vincent J. McGahay, Poughkeepsie, NY (US); Bhupesh Chandra, New York, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 66 days.

(21) Appl. No.: 15/634,397

(22) Filed: Jun. 27, 2017

(65) Prior Publication Data

US 2018/0375494 A1 Dec. 27, 2018

(51) Int. Cl.
| | |
|---|---|
| *H03H 9/56* | (2006.01) |
| *H01L 41/18* | (2006.01) |
| *H03H 3/08* | (2006.01) |
| *H01L 41/257* | (2013.01) |
| *H03H 3/02* | (2006.01) |
| *H03H 9/02* | (2006.01) |

(52) U.S. Cl.
CPC .............. *H03H 9/56* (2013.01); *H01L 41/18* (2013.01); *H01L 41/257* (2013.01); *H03H 3/02* (2013.01); *H03H 3/08* (2013.01); *H03H 9/02015* (2013.01); *H03H 9/02543* (2013.01)

(58) Field of Classification Search
CPC ............................ H01L 41/18; H01L 41/257
See application file for complete search history.

(56) References Cited

U.S. PATENT DOCUMENTS

| | | | | |
|---|---|---|---|---|
| 4,868,444 | A * | 9/1989 | Shibata | H03H 9/02574 310/313 A |
| 5,059,847 | A * | 10/1991 | Tanaka | H03H 9/02574 310/313 A |
| 6,153,268 | A | 11/2000 | Huggins | |
| 7,482,737 | B2 | 1/2009 | Yamada et al. | |
| 7,579,761 | B2 | 8/2009 | Nishihara et al. | |
| 9,425,766 | B2 * | 8/2016 | Fujiwara | H03H 9/02559 |
| 10,063,210 | B2 * | 8/2018 | McCarron | H01J 37/3447 |
| 2016/0225640 | A1 | 8/2016 | Raley et al. | |

OTHER PUBLICATIONS

Lueng, et al., "Piezoelectric coefficient of aluminum nitride and gallium nitride", Journal of Applied Physics; vol. 88, No. 3, Nov. 1, 2000, 4 pages.

* cited by examiner

*Primary Examiner* — Dean O Takaoka
*Assistant Examiner* — Alan Wong
(74) *Attorney, Agent, or Firm* — Anthony Canale; Andrew M. Calderon; Roberts Mlotkowski Safran Cole & Calderon, P.C.

(57) ABSTRACT

The present disclosure relates to semiconductor structures and, more particularly, to artificially oriented piezoelectric films for integrated filters and methods of manufacture. The structure includes: a piezoelectric film with effective crystalline orientations of the polar axis rotated 90 degrees from a natural orientation for planar deposited films; and a conductor pattern formed on a surface of the piezoelectric film.

8 Claims, 5 Drawing Sheets

ARTIFICIALLY ORIENTED PIEZOELECTRIC FILM FOR INTEGRATED FILTERS

FIELD OF THE INVENTION

The present disclosure relates to semiconductor structures and, more particularly, to artificially oriented piezoelectric films for integrated filters and methods of manufacture.

BACKGROUND

Piezoelectric films provide the ability to generate an electric charge in response to applied mechanical stress and vice versa. The piezoelectric films can be used in many applications including, e.g., filters.

Piezoelectric planar thin films often have strong vertical coupling, but weak lateral coupling, e.g., AlN. Filters designed using vertical coupling of such a planar thin film are sensitive to film thickness variation. On the other hand, filters designed using lateral coupling are insensitive to film thickness variation but are hampered by weak piezo response.

SUMMARY

In an aspect of the disclosure, a structure comprises: a piezoelectric film with effective crystalline orientations with a polar axis rotated 90 degrees from a natural orientation for planar deposited films; and a conductor pattern formed on a surface of the piezoelectric film.

In an aspect of the disclosure, a method comprises: forming a piezoelectric film with effective crystalline orientations with a polar axis rotated 90 degrees from a natural orientation for planar deposited piezoelectric films; and forming electrodes on a planar surface of the piezoelectric film.

In an aspect of the disclosure, a method comprises: depositing a mandrel film on a substrate; patterning the mandrel film to form alternating lines and spaces; depositing a first piezoelectric film over surfaces of the patterned mandrel film including sidewalls within the spaces; removing excess first piezoelectric film to expose the patterned mandrel film; removing of the patterned mandrel film; depositing of a second piezoelectric film over the first piezoelectric film including sidewalls formed by removing of the patterned mandrel film; removing excess second piezoelectric film to expose the first piezoelectric film such that the first and second piezoelectric films have crystal orientations with a polar axis determined by growth from the sidewalls; and patterning conductor material on the first and second piezoelectric films.

BRIEF DESCRIPTION OF THE DRAWINGS

The present disclosure is described in the detailed description which follows, in reference to the noted plurality of drawings by way of non-limiting examples of exemplary embodiments of the present disclosure.

DETAILED DESCRIPTION

The present disclosure relates to semiconductor structures and, more particularly, to artificially oriented piezoelectric films for integrated filters and methods of manufacture. More specifically, the present disclosure provides a piezoelectric film used in a planar electrode configuration with a strong lateral piezoelectric response. That is, the present disclosure provides a planar film structure with strong lateral piezoelectric coupling, which does not naturally occur for piezoelectric material, e.g., aluminum nitride, deposited using conventional thin film techniques. Accordingly and advantageously, the structures described herein provide superior filter operation due to strong piezoelectric response, with reduced sensitivity to geometric variation.

In embodiments, the artificially oriented piezoelectric film can be manufactured using spacer/mandrel processes to create a planar film configuration with strong lateral piezoelectric coupling. In embodiments, mandrel processes can be used to form alternating piezoelectric spacers. More specifically, the mandrel/spacer processes are used to form a piezoelectric film with an artificially achieved crystallographic orientation of the polar axis, e.g., rotated 90 degrees from a naturally occurring orientation, by exploiting preferred growth habits of the piezoelectric film material.

The piezoelectric film with artificially achieved crystallographic orientation of the present disclosure can be manufactured in a number of ways using a number of different tools. In general, though, the methodologies and tools are used to form structures with dimensions in the micrometer and nanometer scale. The methodologies, i.e., technologies, employed to manufacture the piezoelectric film with artificially achieved crystallographic orientation of the present disclosure have been adopted from integrated circuit (IC) technology. For example, the piezoelectric film with artificially achieved crystallographic orientation can be built on wafers and are realized in films of material patterned by photolithographic processes on the top of a wafer. In particular, the fabrication of the piezoelectric film with artificially achieved crystallographic orientation uses four basic building blocks: (i) deposition of thin films of material on a substrate, (ii) applying a patterned mask on top of the films by photolithographic imaging, (iii) etching the films selectively to the mask, and (iv) removal of excess or sacrificial thin film materials, e.g. by wet etching, dry etching, or polish.

Figure 1A:
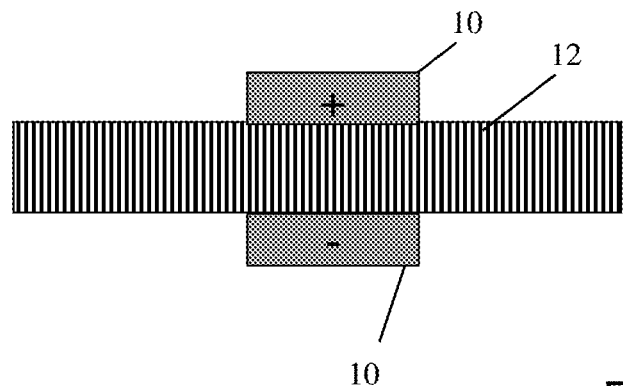
FIGS. 1A and 1B show different piezoelectric thin film configurations.
Figure 1B:
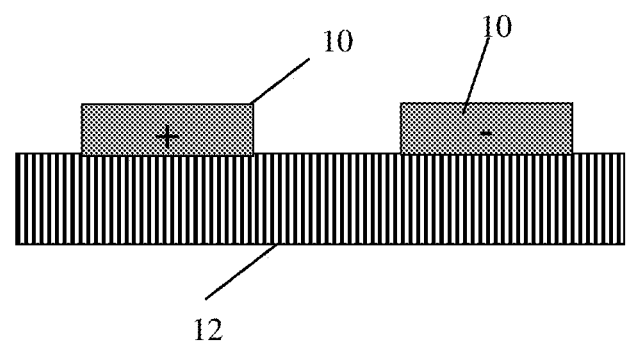

FIGS. 1A and 1B show different piezoelectric thin film configurations. In particular, FIG. 1A shows electrodes 10 on a top surface and bottom surface of a piezoelectric film 12, e.g., AlN. In this representation, the piezoelectric film 12 has a vertical crystalline orientation for the polar axis, which provides strong vertical coupling but weak lateral coupling. This piezoelectric film configuration also has a high thickness sensitivity. As should be understood, the piezoelectric film 12 grows in certain crystallographic directions, i.e., 001 direction or 111 direction, which are known as the polar axes, hence exhibiting piezoelectric properties.

FIG. 1B, on the other hand, shows electrodes 10 in a planar configuration, e.g., on a top surface of the piezoelectric film 12. In this configuration, the piezoelectric film 12 also has a vertical crystalline orientation, but now has a weak piezo response due to the planar topography of the electrode configuration. The structure of FIG. 1B, though, has a low thickness sensitivity.

Figure 2:
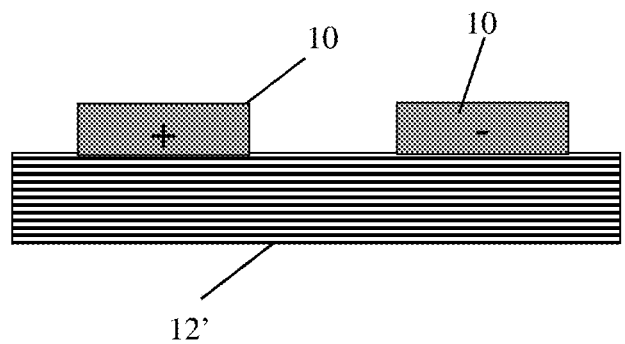
FIG. 2 shows a planar electrode configuration with a strong lateral response in accordance with aspects of the present disclosure.

FIG. 2 shows a planar electrode configuration with a strong lateral piezoelectric response in accordance with aspects of the present disclosure. In particular, FIG. 2 shows electrodes 10 in a planar configuration, e.g., on a surface of the piezoelectric thin film 12', e.g., AlN. In embodiments, the piezoelectric thin film 12' has a horizontal crystalline orientation, e.g., a piezoelectric film with effective crystalline orientations of the polar axis rotated 90 degrees from the natural orientation for planar deposited films. In other words, the piezoelectric film 12' has its crystallographic directions oriented horizontally to provide a strong piezoelectric response. It needs to be recognized that the horizontal crystalline orientation of the piezoelectric thin film 12' is an artificially achieved crystallographic orientation caused by exploiting preferred growth habits of the material as described herein. In this way, it is possible to provide a conductor pattern formed on a planar surface (e.g., top surface) of the piezoelectric film 12' to create an electrical filter that has strong piezo coupling and low thickness sensitivity.

Although described in more detail below, the method of forming the artificially oriented planar piezoelectric film 12' with enhanced piezoelectric response comprises: (i) planar deposition of a non-piezoelectric film (substrate 12'); (ii) planar deposition of a mandrel film over the non-piezoelectric film; (iii) patterning of the mandrel film to form alternating lines and spaces; (iv) deposition of a first piezoelectric thin film over all exposed surfaces of the patterned mandrel film including sidewalls; (v) removal of excess first piezoelectric film to expose the patterned mandrel film; (vi) removal of the patterned mandrel film; (vii) deposition of a second piezoelectric thin film over all exposed surfaces of the first piezoelectric film including sidewalls; and (viii) removal of excess second piezoelectric film to expose the first piezoelectric film such that the remaining first and second piezoelectric films have crystal orientations determined by growth of from sidewalls. A conductor pattern can be formed on the first and second piezoelectric films, which has crystal orientations in a horizontal orientation.

Figure 3A:
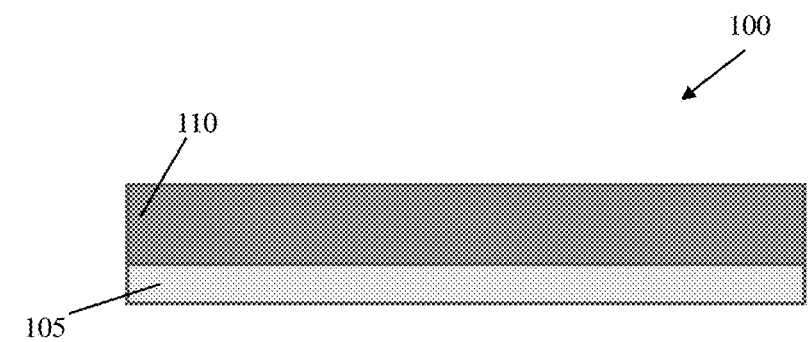
FIGS. 3A-3H show fabrication processes and respective structures for manufacturing of an artificially oriented piezoelectric film for integrated filters in accordance with aspects of the present disclosure.

FIGS. 3A-3H show fabrication processes and respective structures for manufacturing of an artificially oriented piezoelectric film for integrated filters in accordance with aspects of the present disclosure. In particular, FIG. 3A shows an incoming structure 100 comprising a substrate 105 and a mandrel material 110. In embodiments, the substrate 105 can be an insulating substrate, e.g., oxide or other insulator material. The mandrel material 110 can be polysilicon or metal material, as examples. The mandrel material 110 should have a thickness which effectively allows the crystal orientation of piezoelectric films to change from a vertical orientation of the polar axis to a horizontal orientation, e.g., resulting in an artificially achieved crystallographic orientation. For example, the thickness of the mandrel material 110 can be, e.g., 100 nm to 1000 nm.

Figure 3B:
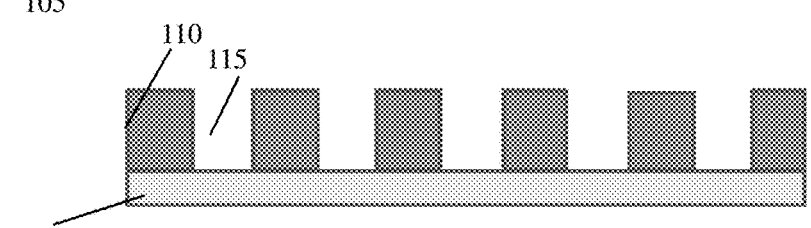

As shown in FIG. 3B, the mandrel material 110 is patterned using conventional lithographic and etching processes. In embodiments, the patterning process can be a timed etch process, as an example. Illustratively and as a non-limiting example, a resist formed over the mandrel material 110 is exposed to energy (e.g., light) to form a pattern (openings). An etching process with a selective chemistry, e.g., reactive ion etching (RIE), is performed through the openings to remove mandrel material, forming spaces 115 between the remaining mandrel material 110. The resist can then be removed by a conventional oxygen ashing process or other known stripants. In embodiments, the spaces 115 can be of any appropriate size, e.g., 100 nm to 1000 nm, to allow the crystal orientation of piezoelectric films to change from a vertical orientation to a horizontal orientation, as described herein.

Figure 3C:
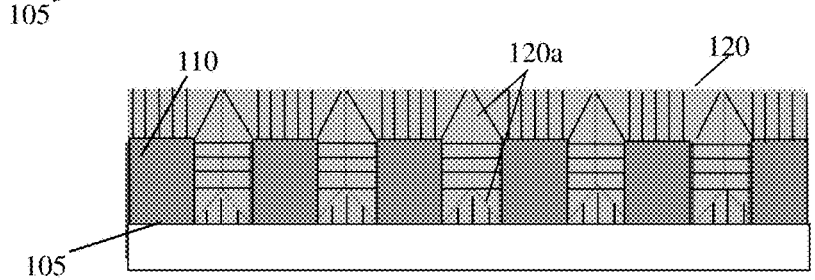

In FIG. 3C, a piezoelectric film 120 is deposited within the spaces 115 and over the mandrel material 110. In embodiments, the piezoelectric film 120 can be AlN, deposited using conventional deposition processes. For example, the piezoelectric film 120 can be deposited using a conventional chemical vapor deposition (CVD), plasma enhanced CVD (PECVD), atomic layer deposition (ALD) or a sputter deposition.

As shown in FIG. 3C, the crystal orientation of the piezoelectric film 120 changes from a vertical orientation of the polar axis to a horizontal orientation, e.g., artificially achieved crystallographic orientation, as demarcated by the seams 120a and as shown representatively by the horizontal and vertical lines. Specifically, as should be understood by those of ordinary skill in the art, the growth process of the piezoelectric film 120 will result in a crystal orientation of the polar axis of 90 degrees (i.e., perpendicular) to the vertical surfaces of the sidewalls of mandrel material 110 (represented by the horizontal lines), and a crystal orientation of 90 degrees to the horizontal surface of the substrate 105 (represented by the vertical lines). In this way, specifically, the crystal orientation at the upper portions of the piezoelectric film 120, e.g., between an upper portion of the mandrel material 110 and above, will be in a horizontal (or lateral) orientation (i.e., artificially achieved crystallographic orientation), compared to a vertical orientation at the substrate 105.

Figure 3D:
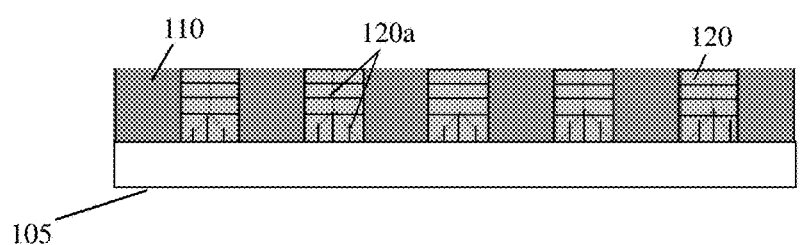

In FIG. 3D, the piezoelectric film 120 will be planarized, e.g., to be planar with and exposing an upper surface of the mandrel material 110, by undergoing a conventional chemical mechanical polishing (CMP) or a dry etch process. For example, the dry chemistry for AlN removal may be: $BCl_3/Cl_2/Ar$; $SF_6/Ar$; $CH_4/H_2/Ar$; or $Cl_2/H_2$ ECR (Electron Cyclotron Resonance). The CMP process may include a slurry comprising, e.g., $SiO_2$ particles in $H_2O_2/H_2O$. In embodiments, the planarization process will leave upper portions of the piezoelectric film 120 between the mandrel material 110 in the horizontal (or lateral) orientation, compared to the vertical orientation at the substrate 105.

Figure 3E:
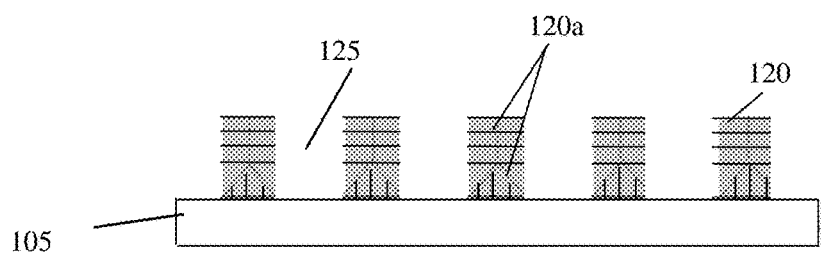
Figure 3F:
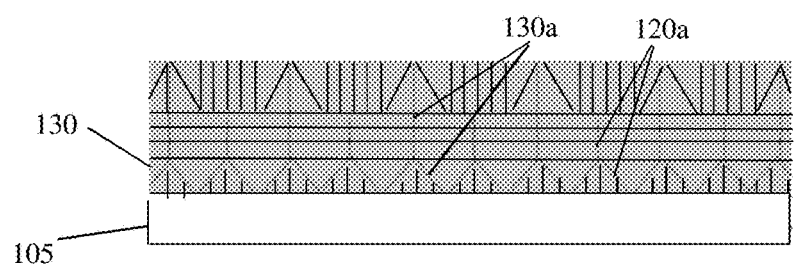

In FIG. 3E, the mandrel material 110 is removed by a selective etching process. For example, the mandrel material 110 can be removed by a Tetramethylammonium hydroxide (TMAH) process with an approximate 20:1 equivalent etch rate. In this way, only the piezoelectric film 120 will remain on the substrate 105, with spaces 125 therebetween (alternating lines 110 and spaces 125). The spaces 125 will expose the underlying substrate 105.

As shown in 3F, another layer of piezoelectric film 130 is deposited on the exposed substrate 105 and over the piezoelectric film 120, using conventional deposition processes, e.g., CVD, PECVD, ALD or a sputter deposition. Due to the piezoelectric film 120 remaining on the substrate 105, the crystal orientation of the piezoelectric film 130 will change from a vertical orientation (near the substrate 105) to a horizontal orientation, e.g., artificially achieved crystallographic orientation, as demarcated by the seams 130a and as shown representatively by the horizontal and vertical lines. Specifically, as with the piezoelectric film 120, the growth process of the piezoelectric film 130 will result in a crystal orientation of the polar axis of 90 degrees (i.e., perpendicular) to the vertical surfaces of the sidewalls of the piezoelectric film 120 (represented by the horizontal lines), and a crystal orientation of 90 degrees to the horizontal surface of the substrate 105 (represented by the vertical lines). In this way, specifically, the crystal orientation at the upper portions of the piezoelectric film 130, e.g., between an upper portion of the mandrel material 110 and above, will be in a horizontal (or lateral) orientation (i.e., artificially achieved crystallographic orientation), compared to a vertical orientation at the substrate 105.

Figure 3G:
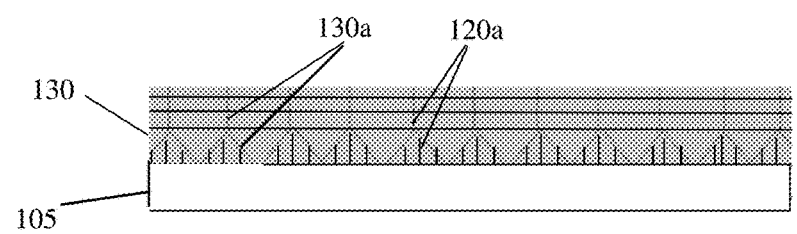

As shown in FIG. 3G, the piezoelectric film 130 will be planarized to a surface of the piezoelectric film 120. In embodiments, the planarization process can be, e.g., a conventional CMP or a dry etch process as described herein. In embodiments, the planarization process will leave upper portions of the piezoelectric films 120, 130 that are in the horizontal (or lateral) orientation, compared to the vertical orientation at the substrate 105. In embodiments, the artificially achieved crystallographic orientation of both piezoelectric films 120, 130 should extend to a desired depth in order to ensure a desired piezo response. For example, the desired depth may be based on the depth of the electrical field lines (of the electrodes 135 shown in FIG. 3H), e.g., a depth of about 100 nm to 1000 nm.

Figure 3H:
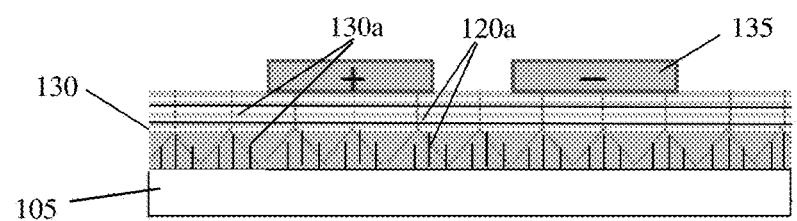

FIG. 3H shows electrodes 135 formed on a surface of the piezoelectric films 120, 130. In more specific embodiments, the electrodes 135 are formed on a planar surface, e.g., same surface, of the piezoelectric films 120, 130. The electrodes 135 can be composed of different materials including, e.g., Al, TiN, Ta, TaN, or Cu based wires with combinations thereof. The electrodes 135 can be formed by conventional deposition, lithography and etching processes, as described herein.

Figure 4A:
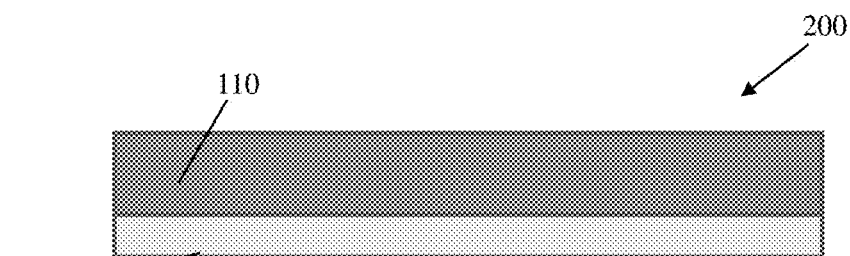
FIGS. 4A-4J show fabrication processes and respective structures for manufacturing of an artificially oriented piezoelectric film for integrated filters in accordance with additional aspects of the present disclosure.

FIGS. 4A-4J show fabrication processes and respective structures for manufacturing of an artificially oriented piezoelectric film for integrated filters in accordance with additional aspects of the present disclosure. In particular, FIG. 4A shows an incoming structure 200 comprising a substrate 105 and a mandrel material 110 similar to that described with reference to FIG. 3A. For example, the substrate 105 can be an insulating substrate, e.g., oxide or other insulator material; whereas, the mandrel material 110 can be polysilicon or metal material. As noted with each aspect described herein, the mandrel material 110 should have a thickness which effectively allows the crystal orientation of piezoelectric films to change from a vertical orientation of the polar axis to a horizontal orientation, e.g., resulting in an artificially achieved crystallographic orientation.

Figure 4B:
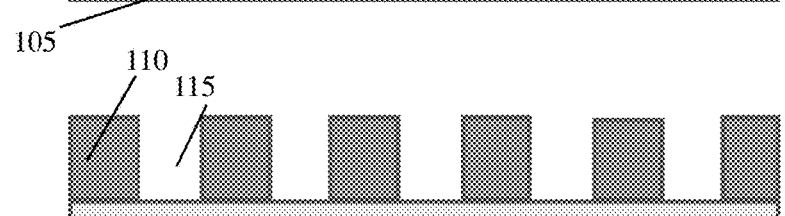

As shown in FIG. 4B, the mandrel material 110 is patterned using conventional lithographic and etching processes. In embodiments, the patterning process can be a timed etch process, as an example, forming spaces 115 between remaining mandrel material 110. In embodiments, the spaces 115 can be of any appropriate size as already described to allow the crystal orientation of piezoelectric films to change from a vertical orientation to a horizontal orientation.

Figure 4C:
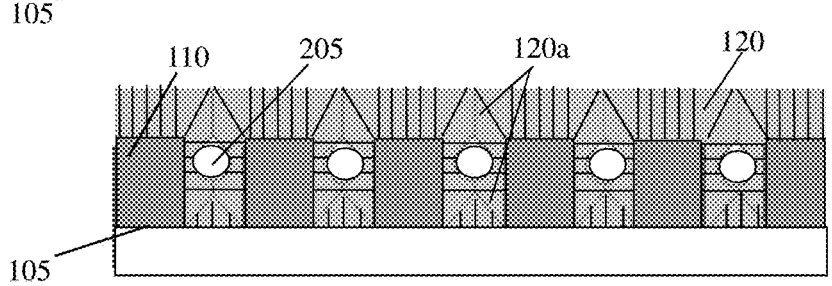

In FIG. 4C, a piezoelectric film 120 is deposited within the spaces 115 and over the mandrel material 110. In embodiments, the piezoelectric film 120 can be AlN, deposited using conventional deposition processes, e.g., CVD, PECVD, ALD or a sputter deposition. The deposition process, though, can result in airgaps (keyhole) 205 due to a pinch off process of the deposited material.

As shown in FIG. 4C, the crystal orientation of the piezoelectric film 120 changes from a vertical orientation of the polar axis to a horizontal orientation, e.g., artificially achieved crystallographic orientation, as demarcated by the seams 120a and as shown representatively by the horizontal and vertical lines. As previously described, the crystal orientation at the upper portions of the piezoelectric film 120, e.g., between an upper portion of the mandrel material 110 and above, will be in a horizontal (or lateral) orientation (i.e., artificially achieved crystallographic orientation), compared to a vertical orientation at the substrate 105.

Figure 4D:
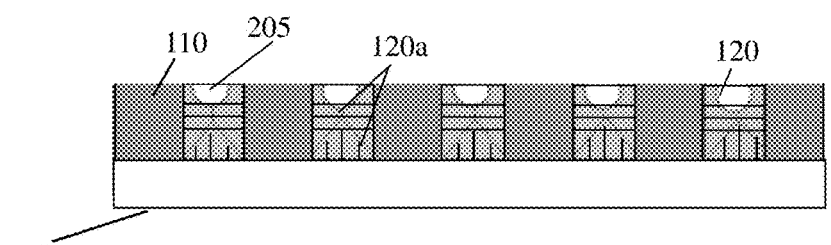

In FIG. 4D, the piezoelectric film 120 will be planarized, e.g., planar with and exposing an upper surface of the mandrel material 110, by undergoing a CMP or a dry etch process as already described herein. In embodiments, the planarization process will open the airgaps 205, but will still leave piezoelectric film 120 between the mandrel material 110 that is in the horizontal (or lateral) orientation, compared to the vertical orientation at the substrate 105.

Figure 4E:
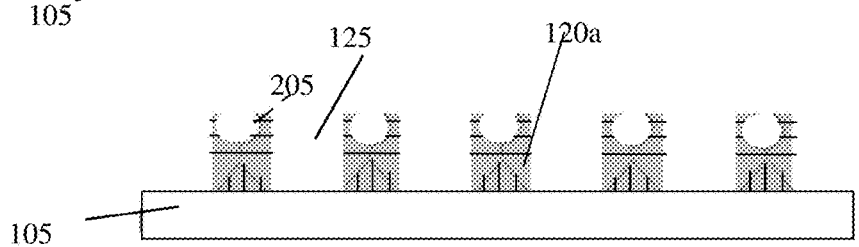
Figure 4F:
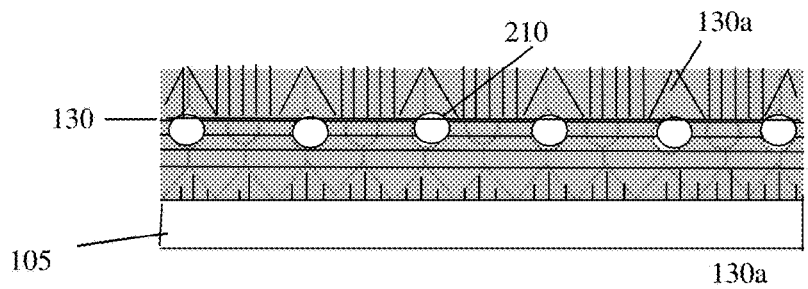

In FIG. 4E, the mandrel material 110 is removed by a selective etching process, e.g., TMAH process with an approximate 20:1 equivalent etch rate. In this way, the piezoelectric film 120 will remain on the substrate 105, with spaces 125 therebetween. The spaces 125 will expose the underlying substrate 105.

As shown in 4F, another layer of piezoelectric film 130 is deposited on the exposed substrate 105, over the piezoelectric film 120 and filling the opened airgaps 205. Due to the piezoelectric film 120 remaining on the substrate 105, the crystal orientation of the piezoelectric film 130 will change from a vertical orientation of the polar axis (near the substrate 105) to a horizontal orientation, e.g., artificially achieved crystallographic orientation, as demarcated by the seams 130a and as shown representatively by the horizontal and vertical lines. Specifically, as with the piezoelectric film 120, the growth process of the piezoelectric film 130 will result in a crystal orientation of the polar axis of 90 degrees (i.e., perpendicular) to the vertical surfaces of the piezoelectric film 120 (represented by the horizontal lines), and a crystal orientation of 90 degrees to the horizontal surface of the substrate 105 (represented by the vertical lines). In this way, specifically, the crystal orientation at the upper portions of the piezoelectric film 130, e.g., between an upper portion of the mandrel material 110 and above, will be in a horizontal (or lateral) orientation (i.e., artificially achieved crystallographic orientation), compared to a vertical orientation at the substrate 105.

Figure 4G:
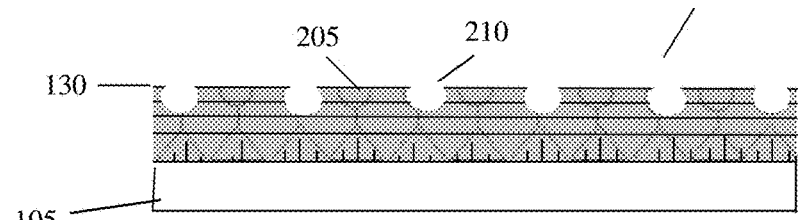

As shown in FIG. 4G, the piezoelectric film 130 will be planarized to a surface of the piezoelectric film 120, opening airgaps 210. In embodiments, the planarization process can be, e.g., a conventional CMP or a dry etch process as described herein. In embodiments, the planarization process will leave upper portions of the piezoelectric films 120, 130 that are in the horizontal (or lateral) orientation of the polar axis, compared to the vertical orientation at the substrate 105.

Figure 4H:
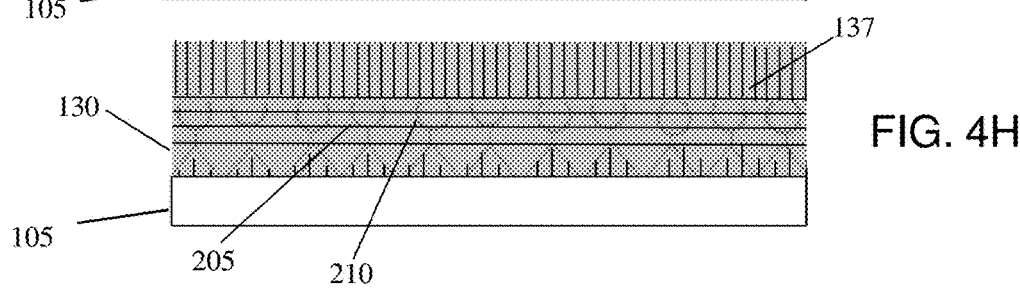

In FIG. 4H, another layer of piezoelectric film 137 is deposited on the piezoelectric film 137, filling the opened airgaps 210. Again it is noted that the crystal orientation of the piezoelectric film 137 will be in a horizontal orientation, e.g., artificially achieved crystallographic orientation, due to the growth on sidewalls of the airgaps 210.

Figure 4I:
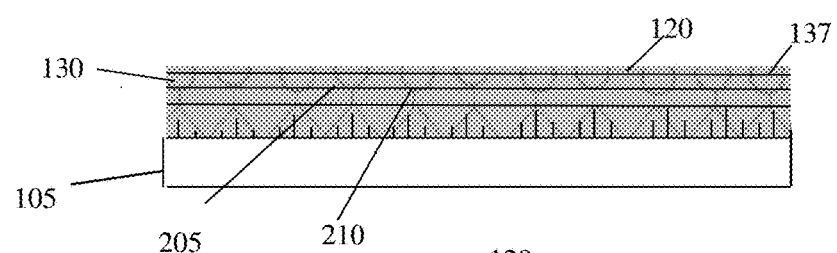

In FIG. 4I, the piezoelectric film 137 will be planarized to a surface of the piezoelectric film 130, leaving the piezoelectric film 137 in the opened airgaps 210. In embodiments, the planarization process can be, e.g., a conventional CMP or a dry etch process as described herein. In embodiments, the planarization process will leave portions of the piezoelectric films 120, 130, 137 that are in the horizontal (or lateral) orientation to a desired depth to ensure a desired piezo response, as described already herein, compared to the vertical orientation at the substrate 105.

Figure 4J:
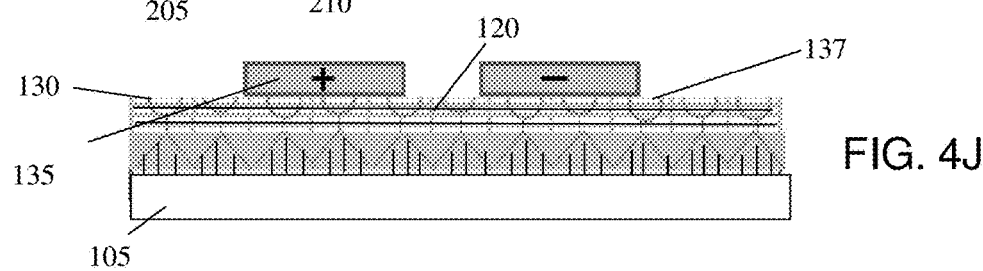

FIG. 4J shows electrodes 135 formed on a surface of the piezoelectric films 120, 130, 137. In more specific embodiments, the electrodes 135 are formed on a planar surface, e.g., same surface, of the piezoelectric films 120, 130, 137. The electrodes 135 can be composed of different materials including, e.g., Al, TiN, Ta, TaN, or Cu based wires with combinations thereof. The electrodes 135 can be formed by conventional deposition, lithography and etching processes, as described herein.

The method(s) as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A structure comprising:
    a piezoelectric film with effective crystalline orientations of a polar axis rotated 90 degrees from a natural orientation for planar deposited films; and
    a conductor pattern formed on a surface of the piezoelectric film, wherein
    the conductor pattern comprises electrodes formed on a single, planar surface of the piezoelectric film,
    the piezoelectric film has an effective crystalline orientation of the polar axis in a horizontal orientation, with respect to the conductor pattern, and
    the effective crystalline orientations of the polar axis are in a vertical direction adjacent to an underlying substrate.

2. The structure of claim 1, wherein the piezoelectric film is AN.

3. The structure of claim 1, wherein the conductor pattern and piezoelectric film is an electrical filter.

4. The structure of claim 1, wherein the effective crystalline orientations is to a depth of at least an electric field generated by the electrodes.

5. The structure of claim 1, wherein the piezoelectric film fills in airgaps created in an underlying piezoelectric film.

6. The structure of claim 1, wherein the horizontal orientation is an artificial orientation of the piezoelectric film which provides enhanced piezoelectric response in comparison to a film with a vertically oriented polar axis.

7. A structure comprising:
    a piezoelectric film with effective crystalline orientations of a polar axis rotated 90 degrees from a natural orientation for planar deposited films; and
    a conductor pattern formed on a surface of the piezoelectric film,
    wherein the effective crystalline orientations of the polar axis are in a vertical direction adjacent to an underlying substrate.

8. The structure of claim 7, wherein the piezoelectric film has an effective crystalline orientation of the polar axis in a horizontal orientation, with respect to the conductor pattern.

* * * * *

UNITED STATES PATENT AND TRADEMARK OFFICE
CERTIFICATE OF CORRECTION

PATENT NO. : 10,483,943 B2
APPLICATION NO. : 15/634397
DATED : November 19, 2019
INVENTOR(S) : Vincent J. McGahay et al.

It is certified that error appears in the above-identified patent and that said Letters Patent is hereby corrected as shown below:

In the Claims

In Claim 2, Line 16 at Column 8, change "AN" to "AlN".

Signed and Sealed this
Eleventh Day of February, 2020

Andrei Iancu
*Director of the United States Patent and Trademark Office*